(12) United States Patent
Hyde et al.

(10) Patent No.: US 7,361,509 B2
(45) Date of Patent: Apr. 22, 2008

(54) DYNAMIC METERED FLUID VOLUME DETERMINATION METHOD AND RELATED APPARATUS

(75) Inventors: David D. Hyde, Ontario, NY (US); Joseph S. Douglas, Webster, NY (US)

(73) Assignee: Ortho-Clinical Diagnostics, Rochester, NY (US)

( * ) Notice: Subject to any disclaimer, the term of this patent is extended or adjusted under 35 U.S.C. 154(b) by 532 days.

(21) Appl. No.: 10/134,409

(22) Filed: Apr. 29, 2002

(65) Prior Publication Data

US 2003/0203494 A1 Oct. 30, 2003

(51) Int. Cl.
*G01N 35/02* (2006.01)
*G01N 1/10* (2006.01)

(52) U.S. Cl. .................. 436/47; 422/63; 422/64; 422/65; 422/66; 422/67; 422/100; 436/43; 436/46; 436/49; 436/54; 436/180

(58) Field of Classification Search ........... 422/63–67, 422/100; 436/43, 46–47, 49, 54, 180
See application file for complete search history.

(56) References Cited

U.S. PATENT DOCUMENTS

| | | | | |
|---|---|---|---|---|
| 3,614,434 | A * | 10/1971 | Horwitz et al. | 250/364 |
| 3,759,667 | A * | 9/1973 | Bannister et al. | 73/864.22 |
| 3,836,335 | A * | 9/1974 | Eppes | 422/50 |
| 4,130,394 | A * | 12/1978 | Negersmith | 436/179 |
| 4,311,484 | A * | 1/1982 | Fosslien | 73/864.21 |
| 4,399,362 | A * | 8/1983 | Cormier et al. | 250/430 |
| 4,399,711 | A * | 8/1983 | Klein | 73/864.16 |
| 4,517,302 | A * | 5/1985 | Saros | 436/180 |
| 4,780,833 | A * | 10/1988 | Atake | 700/281 |
| 4,818,492 | A * | 4/1989 | Shimizu | 422/100 |
| 4,829,837 | A * | 5/1989 | Telfer | 73/863.01 |
| 5,013,529 | A * | 5/1991 | Itoh | 422/100 |
| 5,045,286 | A * | 9/1991 | Kitajima et al. | 422/100 |
| 5,090,255 | A * | 2/1992 | Kenney | 73/863.02 |
| 5,296,194 | A * | 3/1994 | Igarashi | 422/82.05 |
| 5,319,954 | A * | 6/1994 | Koeda et al. | 73/19.1 |
| 5,443,791 | A * | 8/1995 | Cathcart et al. | 422/65 |
| 5,465,629 | A * | 11/1995 | Waylett, Jr. | 73/864.24 |
| 5,525,514 | A * | 6/1996 | Jacobs et al. | 436/46 |
| 5,537,880 | A * | 7/1996 | Takeda et al. | 73/864.25 |
| 5,554,811 | A | 9/1996 | Rokugawa et al. | |
| 5,601,980 | A * | 2/1997 | Gordon et al. | 435/6 |
| 5,723,795 | A * | 3/1998 | Merriam | 73/863 |

(Continued)

*Primary Examiner*—Arlen Soderquist
(74) *Attorney, Agent, or Firm*—Hiscock & Barclay, LLP

(57) ABSTRACT

A method for dynamically determining the volume of a liquid dispensed by a metering system, the metering system including a metering pump, a pump motor, a sensor, and a conduit interconnecting the pump and a metering probe. The method includes the steps of aspirating a quantity of fluid into the metering probe using the metering pump, moving the probe relative to a reaction vessel, and dispensing the fluid. The dispensing step includes the steps of identifying an onset point associated with a parameter which can be measured by the metering system, identifying an end point associated with the measurable parameter, and timing the pump motor during the period between the onset point and the end point in order to determine fluid volume. The sensor, such as a pressure transducer or capacitance change sensor, disposed in relation to the conduit can detect changes in the parameter and identify the onset and end points.

5 Claims, 3 Drawing Sheets

U.S. PATENT DOCUMENTS

| | | | |
|---|---|---|---|
| 5,724,142 A | * 3/1998 | Kaminski et al. | 356/627 |
| 5,777,221 A | * 7/1998 | Murthy et al. | 73/149 |
| 6,060,320 A | * 5/2000 | Dorenkott et al. | 436/54 |
| 6,121,049 A | * 9/2000 | Dorenkott et al. | 436/50 |
| 6,158,269 A | * 12/2000 | Dorenkott et al. | 73/37 |
| 6,250,130 B1 | * 6/2001 | Howard et al. | 73/1.36 |
| 6,338,820 B1 | * 1/2002 | Hubbard et al. | 422/64 |
| 2001/0016177 A1 | 8/2001 | Pelc et al. | |
| 2001/0047692 A1 | 12/2001 | Lipscomb et al. | |

* cited by examiner

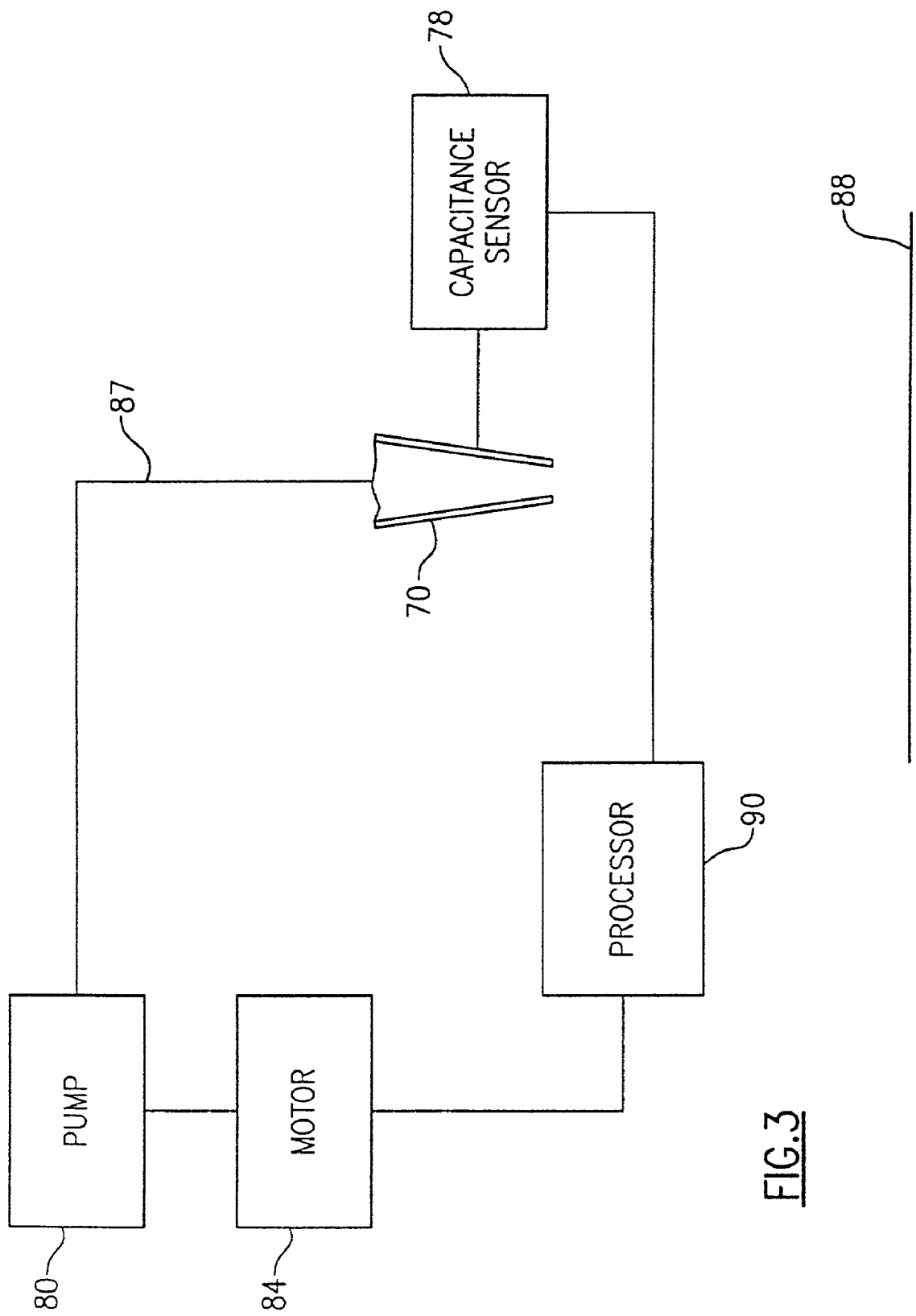

DYNAMIC METERED FLUID VOLUME DETERMINATION METHOD AND RELATED APPARATUS

FIELD OF THE INVENTION

This invention relates generally to the field of clinical analytical systems, and specifically to a method for dynamically determining the volume of a liquid which is metered onto a slide element or other reaction vessel.

BACKGROUND OF THE INVENTION

Automated mainframe and desk-top analytical apparatus are repletely known in the field of clinical chemistry, including those manufactured, for example, by Abbott Laboratories, Ltd., and Ortho Clinical Diagnostics, Inc, among others. Each of these apparatus commonly include at least one metering system which is used to aspirate a quantity of a fluid sample, such as patient fluid, reagent, or calibration and/or wash fluids into a proboscis through a pumping mechanism from a fluid supply for subsequent dispense onto a slide element in the case of so-called dry-chemistry systems or into a reaction well or cuvette in the case of "wet" chemistry systems for subsequent analysis.

In either instance (e.g., wet or dry chemistry analytical system) and for literally any test which is required using such apparatus, it is imperative to have a correct volume of fluid delivered to the reaction vessel. There are various known techniques for ascertaining whether a sufficient fluid volume has been delivered, but these techniques are empirical and any insufficiencies are not realized until additional testing has been conducted. To date, there has been no technique demonstrated to dynamically ascertain fluid volumes.

SUMMARY OF THE INVENTION

It is a primary object of the present invention to overcome the above-noted deficiencies of the prior art.

It is a further primary object of the present invention to develop a method for dynamically determining fluid volumes which have been delivered to a reaction vessel using a clinical analytical metering system.

Therefore and according to a preferred aspect of the invention there is described a method for dynamically determining the volume of a liquid dispensed by a metering system, said metering system including a metering pump and a pump motor, said method including the steps of:

aspirating a quantity of liquid into a metering probe using said metering pump;

moving said metering probe relative to a reaction vessel; and dispensing the quantity of liquid onto said reaction vessel, said dispensing step including the steps of:

identifying an onset point associated with a parameter which can be measured by said metering system;

identifying an end point associated with said parameter; and timing the pump motor between said onset point and said end point.

The metering system includes a conduit interconnecting the metering probe and the metering pump and at least one sensor disposed relative to the conduit for measuring the parameter. According to one embodiment, the sensor includes at least one pressure transducer for measuring pressure changes in the metering probe.

Preferably, a first pressure change is indicative of the onset point and a second pressure change is indicative of the end point.

According to yet another embodiment, the sensor measures capacitance changes in relation to the metering probe. In order to measure these changes, it is preferable that the liquid which is being dispensed be ionic in nature. For example, initiation of liquid flow from the metering probe indicates a first change in capacitance indicative of the onset point and cessation of liquid flow from the metering probe indicates a second change in capacitance indicative of the end point. Each of the preceding capacitance changes are drastic (ie., rapid) in nature, whereas steady state events, such as liquid flow during the dispense/metering process, do not create a discernible capacitance change.

In the instance in which the pump motor is a stepper motor, the timing step includes the step of counting the number of motor pulses between the onset point and the end point in that each pulse (assumed constant) relates to a constant displacement of liquid which is delivered to the reaction vessel. Therefore, counting the number of pulses provides a determination of fluid volume. It should be apparent that the determination (identification) of the check points is the essential aspect of the invention. Therefore, other techniques for measuring volume during the period between the onset point and the end point can be utilized once these "trigger" points have been established. For example, any means for measuring the displacement (output) of the motor can be used over that period in order to determine fluid output.

According to another preferred aspect of the present invention, there is disclosed an apparatus for dynamically determining the volume of a liquid dispensed by a metering system, said metering system including a metering pump and a pump motor whereby a quantity of liquid is aspirated into a metering probe and dispensed onto a reaction vessel using said metering pump, said apparatus comprising:

means for identifying an onset point associated with a parameter which can be measured by said metering system;

means for identifying an end point associated with said parameter; and means for timing the pump motor between said onset point and said end point.

According to yet another preferred aspect of the present invention, there is disclosed a method for dynamically determining the volume of a wash liquid dispensed by a metering system onto an immuno-rate slide element, said metering system including a metering pump having a displacement element and a pump motor, said method including the steps of:

aspirating a quantity of wash liquid into a metering probe using said metering pump;

moving said metering probe relative to said slide element; and dispensing the quantity of liquid onto said slide element, said dispensing step including the steps of:

identifying an onset point associated with a parameter which can be measured by said metering system;

identifying an end point associated with said parameter; and measuring the displacement of the pump displacement element between said onset point and said end point in order to determine volume.

According to still another preferred aspect of the present invention, there is described an apparatus for dynamically determining the volume of a wash liquid dispensed by a metering system onto an immuno-rate slide element, said metering system including a metering pump having a displacement element and a pump motor whereby a quantity of wash liquid is aspirated into a metering probe and dispensed onto the slide element using said metering pump, said apparatus comprising:

means for identifying an onset point associated with a parameter which can be measured by said metering system;

means for identifying an end point associated with said parameter and;

means for measuring the displacement of the pump displacement element between said onset point and said end point.

An advantage of the present invention is that fluid metered volumes can now be determined dynamically, thereby significantly improving the reliability of clinical analytical apparatus.

Another advantage is that the volume measurement methods described herein can be incorporated into literally any metering system having at least one metering pump, a metering probe and a conduit therebetween permitting the inclusion of a sensor in relation to the conduit.

Yet another advantage is that flow uniformity during the dispense phase of a metering event can be more effectively monitored. That is to say, occurrences which prevent smooth delivery of fluid an be identified and detected.

These and other objects, features, and advantages will become readily apparent from the following Detailed Description which should be read in conjunction with the accompanying drawings.

BRIEF DESCRIPTION OF THE DRAWINGS

FIG. 3 is a schematic view of a metering system having an alternate sensor embodiment which includes a capacitance level sense system.

DETAILED DESCRIPTION

The following description relates to a specific metering system for an immuno-rate (IR) wash module used with a mainframe clinical analytical device. It will become readily apparent from this description, however, that the inventive concepts are applicable to literally any metering system.

Figure 1:
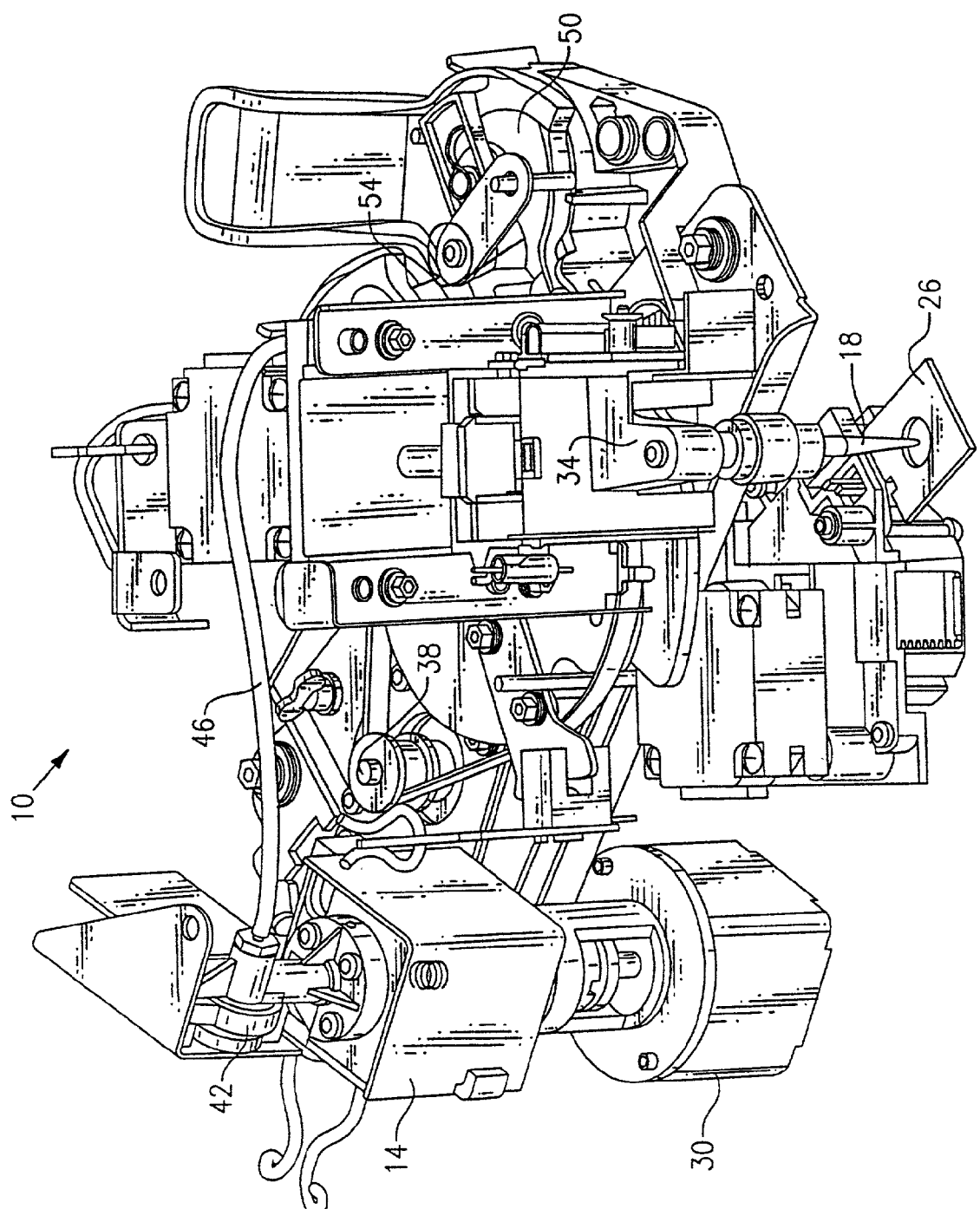
FIG. 1 is a partial top perspective view of a metering system for a clinical analytical apparatus.

For purposes of this discussion and referring to FIG. 1, analytical slide elements, such as immuno-rate (IR) slides, use the principle of antigens and antibodies to detect the levels of therapeutic drugs and to diagnose diseases. The slides use a complex chemical reaction to identify and measure the concentration of an analyte in a sample fluid. To calculate the test results, a reflectometer or other device is then used to verify the changing color of the slide. Specifics relating to the chemistry and the testing are already well known in the field and do not form a part of the present invention.

In terms of the wash module, however, and after a patient sample has been delivered to the IR slide, the slide must be washed. The slide is incubated for a predetermined period of time and then a wash liquid is applied.

FIG. 1 illustrates the IR wash module 10 which includes a metering pump 14 which includes a motor 30, the pump being a positive displacement (piston) pump and a sensitive pressure transducer 42 which is common to the internal volume of the piston pump system. By using a plurality of system amplifiers, the pressure differences created by the piston pump during the IR wash metering cycle can be monitored and used for input for the central of fluid delivery.

A metering probe 18 includes a proboscis which is interconnected to the metering pump 14 by means of a flexible conduit 46. A disposable conical metering tip (not shown) such as those manufactured by Johnson and Johnson Company under the tradename of Vitros™ is attached onto the proboscis for each metering event. The metering probe 18 is movable relative to a pair of fluid reservoirs 50, 54 by means of a pair of motor control mechanisms 34, 38 which control angular and vertical movement, respectively. The specifics of these mechanisms are commonly known in the field, for example, the angular motor control mechanism 38 employs a drive belt 58 and gear connection, and do not require further discussion except as needed for purposes of the present invention.

The presently described wash module 10 requires a fluid volume of 12 micro-liters to be delivered to a slide element 26 over a 15 second period. This yields a fluid delivery rate of about 0.8 micro-liters/second.

Figure 2:
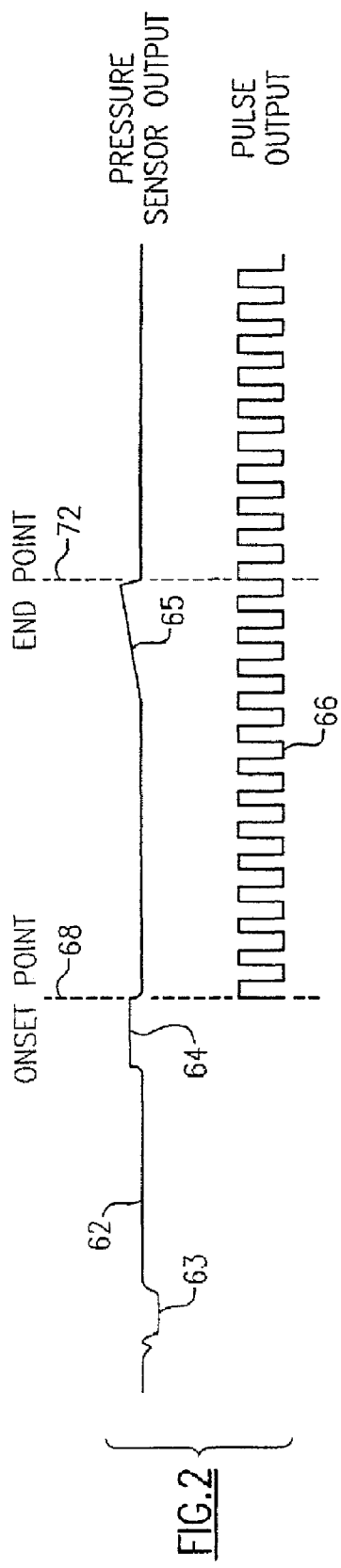
FIG. 2 is a diagrammatic view of the output signal of a pressure transducer of the metering system of FIG. 1 as used to trigger an onset point and end point for dynamically calculating fluid volume using the pulse output of the metering pump motor.

The wash cycle begins when the metering pump 14 and the accompanying metering probe 18, such as a metering tip, attached to the proboscis, is positioned over an IR wash fluid reservoir 50, 54. The probe 18 is lowered in the vertical (hereinafter referred to as the "Z" direction) by the vertical motor control mechanism 34 towards the surface of the wash fluid. The metering pump 14 has been positioned in a "home" position prior to the start of any Z-direction motion. When the Z-position of the metering probe 18 is near the surface of the wash fluid, the metering pump 14 begins to aspirate. During this aspiration, only air is drawn in. The pressure transducer 42 and its associated hardware (microprocessor) monitor pressure changes as shown in FIG. 2. When the tip of the metering probe 18 penetrates the surface of the fluid, the pressure transducer 42 detects a resistance to flow by a decrease in pressure, shown pictorially by spike 63. As a result, the resident software analyzes this data and stops the downward Z-motion of the metering probe/tip 18. The metering pump 14 stops motion as soon as the pressure spike 63 is detected.

After a slight delay, the metering pump 14 begins aspiration of the wash fluid. The metering pump 14 actually aspirates more liquid than is required (e.g., about 3 micro-liters) to wash the IR slide 26. This "over aspirate" is dispensed out of the metering probe 18, back into the reservoir 50, 54 in a reversal of the metering pump 14 in order to load the mechanics in preparation for the wash dispense phase. At this time in the cycle, the metering probe "tip" contains the amount of IR wash fluid needed to wash the slide 26. The aspiration of the wash fluid is now complete and the angular and vertical motor control mechanisms 34, 38, respectively, now move the metering probe 18 over the IR slide 26 which is loaded into position synchronously by a slide shuttle mechanism (not shown).

The vertical motor control mechanism 34 moves the metering probe 18 downwardly to a safe position over the IR slide 26. The metering pump 18 displaces a small quantity of liquid (e.g. about one micro-liter) to form a positive meniscus of wash fluid on the tip of the probe 18. This positive meniscus is used to sense the position of the probe 18 along the Z-direction (axis) relative to the IR slide 26. The pressure transducer 42 detects the drop in pressure when the meniscus touches the surface of the slide 26. As soon as this pressure spike is detected, the pump 14 begins the displacement which dispenses wash fluid onto the slide 26.

Referring to FIG. 2, the output signal 62 of the pressure transducer 42 is depicted over the course of the metering cycle in order to better illustrate the present invention. The initial resistance during wash aspiration is shown at 63 in FIG. 2 and the formation of the meniscus and the resulting drop in pressure when the meniscus touches the slide 26 is shown as spike 64.

The above-referred to pressure spike 64 also provides a means for identifying an onset point, shown pictorially in FIG. 2 as 68, to begin timing the pump motor 30. The number of pulses 66 of the pump motor 30 can be counted, assuming the displacement of fluid is known (for example, one pulse according to this embodiment is equivalent to a predetermined amount of fluid). Therefore, counting the total number of pulses will provide an indication of the volume of fluid dispensed.

When all of the wash liquid is dispensed out of the metering probe 18, the pressure inside the pump and the metering probe 18 will drop dramatically because of the differences in the fluid properties between the IR wash liquid and air. Air has much less resistance to flow as compared to the wash fluid, therefore the pressure will be reduced dramatically after all of the wash fluid is dispensed, as shown by spike 65. Due to the real-time monitoring of both the pressure transducer 42 and the steps of the pump motor 30, the end point, shown pictorially as 72, can be exactly identified and timing ceases. The perceived upward ramping of pressure prior to the dramatic drop in pressure shown in FIG. 2 is based upon the geometry of the metering tip which produce surface tension effects.

By all practical means, the metering pump 14 will displace wash fluid in a linear fashion; that is, for every microliter of air displaced by the pump, one microliter of wash fluid will be dispensed. By comparing the pressure drop to the step count, the volume of the wash can be determined. Preferably, if the volume of the wash fluid is below a preset limit (defined by a predetermined number of step counts in this instance), a signal is sent through software to the central computer of the analyzer, flagging the specific test element with an error condition.

Figure 4:
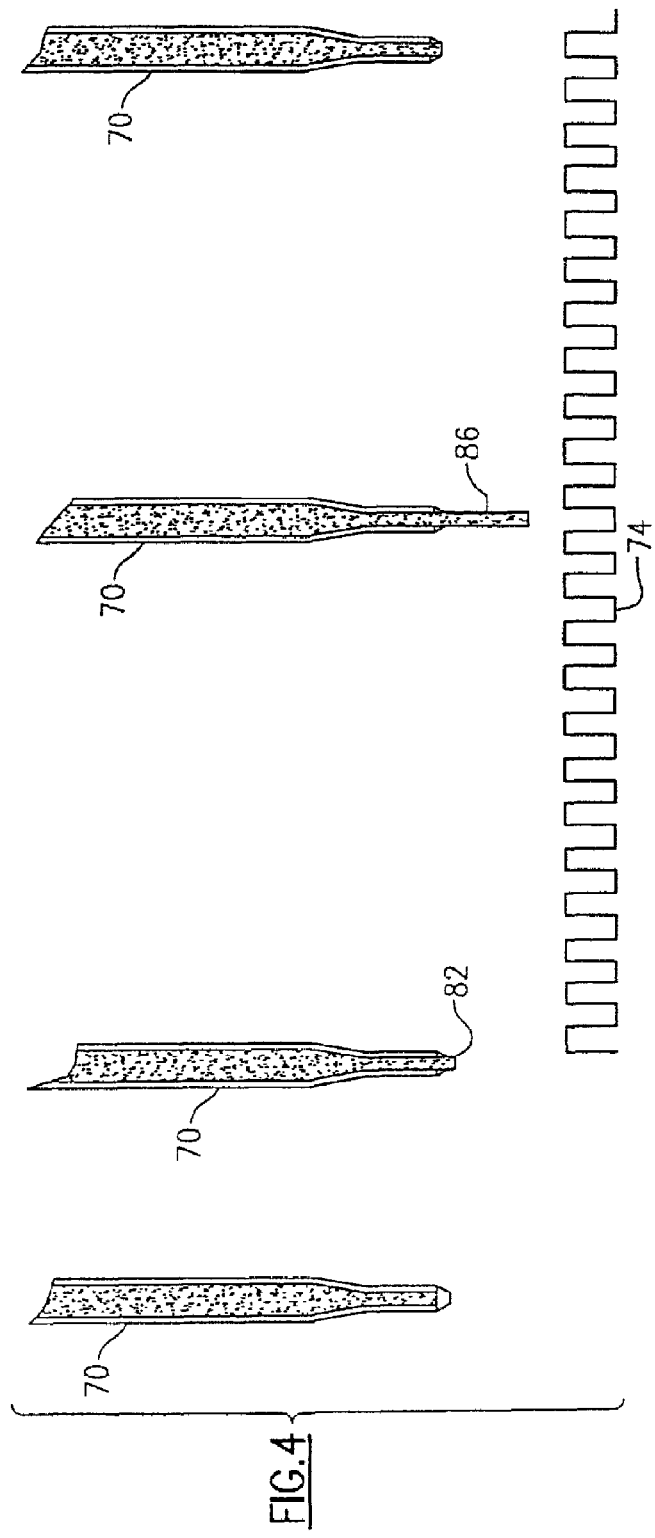
FIG. 4 depicts a series of time-phased sectional views of a metering probe during a metering event using the sensor embodiment of FIG. 3 to compute fluid volume dynamically using the pulse output of the metering pump motor.

Referring to FIGS. 3 and 4, a similar fluid volume determination can be made using other parameter measurement apparatus. For example, and in lieu of using a pressure transducer such as described above in connection with FIGS. 1 and 2, a metering system equipped with a capacitance level sensing system can be used to identify trigger points. Such systems are currently known, such as those presently utilized in the ECi Clinical analyzer manufactured by Ortho Clinical Diagnostics, Inc and those, such as the MSP 9000 and MSP 9250 Sample Processors manufactured by Tecan Systems of San Jose, Calif., and those manufactured by Hamilton Company of Reno, Nev.

A schematic diagram is presented in FIG. 3 of the metering system according to this embodiment. The metering system includes a metering pump 80 which includes a metering pump motor 84. As in the preceding embodiment, the pump 80 is a positive displacement (piston) pump and the motor 84 is a stepper motor, though other designs can be used. A conduit 87 physically interconnects the metering pump 80 with a metering probe 70 (partially shown), similar to that previously described. A capacitance sensor 78 is connected to the metering probe 70, the sensor being further disposed in relation to a ground plane 88, such as, for example, the incubator support, and further connected to a processor 90, the processor also being connected to the pump motor 84.

For purposes of this embodiment, the metering system is used in an IR wash module such as previously shown in FIG. 1, therefore, the metering system would further include elements including at least one fluid reservoir and motor control movement mechanisms. In the present instance and in order to detect capacitance changes, the wash fluid is conductive so as to form an ionic buffer. A quantity of wash fluid is aspirated using the metering pump 80 into the metering probe 70 in the manner previously described and the metering probe is then aligned relative to a reaction vessel which is provided on the ground plane 88, such as a slide holder (not shown).

Referring to FIG. 4, the capacitance sensor 78 senses an increase in mass as a fluid meniscus 82 is initially dispensed from the metering probe 70. This rapid sensed increase in mass of the conductive fluid causes a corresponding and perceivable change in capacitance. This change further identifies a corresponding onset point to begin timing of the pump motor 84. As noted above, the pump motor 84 is a stepper motor and therefore the number of step pulses 74 are counted starting at the above referred to onset point. Following the initial capacitance change, the capacitance tends to level out to a steady state as a steady fluid stream 86 is discharged from the metering probe 70. It should be noted that the quantitative state of the capacitance is not critical to this analysis or to the onset step, merely the change therein.

Following dispense of the fluid from the metering probe 70, another corresponding or resulting change in capacitance occurs as the volume is rapidly decreased due to the breaking off of the fluid column when the motion of the pump piston is stopped. This rapid break in the fluid column causes another capacitance change which identifies the corresponding end point as shown in FIG. 4 at which the counting of motor pulses 74 is stopped.

Utilizing the software, the capacitance changes noted at the start and stop of the dispense part of the process are compared to the number of steps to the stepper motor for dynamic volume verification.

It should be readily apparent that other parameters could be measured using the above-noted approach/concepts. For example, total displacement of fluid could be measured by identifying respective start (onset) and stop (offset) points relative to optical measurement apparatus (not shown).

While the present invention has been particularly shown and described with reference to the preferred mode as illustrated in the drawing, it will be understood by one skilled in the art that various changes in detail may be effected therein without departing from the spirit and scope of the invention as defined by the claims.

Stated most simply, the concepts which have been described herein are applicable to literally any metering system having a positive displacement metering pump, a metering probe, and a conduit interconnecting the metering probe and the pump wherein a sensor which can identify a change in a measurable parameter is placed in relation to the conduit to monitor the parameter. By understanding characteristics of the parameter relative to the metering event, trigger points can therefore be identified for providing a measurement period whereby volume can be determined in real time.

| PARTS LIST FOR FIGS. 1–4 | |
|---|---|
| 10 | IR wash module |
| 14 | metering pump |
| 18 | metering probe |
| 26 | slide element |
| 30 | metering pump motor |
| 34 | vertical motor control mechanism |
| 38 | angular motor control mechanism |
| 42 | pressure transducer |
| 46 | flexible conduit |
| 50 | fluid reservoir |
| 54 | fluid reservoir |
| 58 | drive belt |
| 63 | pressure signal output portion |
| 64 | pressure signal output portion |
| 65 | pressure signal output portion |
| 62 | pressure output signal |
| 66 | pulse output control |
| 68 | onset point |
| 70 | monitoring probe |
| 72 | end point |
| 74 | pulse output signal |
| 78 | capacitance sensor |
| 80 | pump |
| 82 | meniscus |
| 84 | motor |
| 86 | liquid stream |
| 87 | conduit |
| 88 | ground plane |
| 90 | processor |

We claim:

1. A method for dynamically determining the volume of a liquid dispensed by a metering system, said metering system including a metering pump, a metering probe, a conduit between said metering probe and said metering pump, a pump motor and at least one sensor disposed in relation to said conduit for measuring a parameter of said metering system, said pump motor having a positive displacement element, said method including the steps of:

aspirating a quantity of liquid into said metering probe using said metering pump;

moving said metering probe relative to a reaction vessel; and dispensing the quantity of liquid onto said reaction vessel, said dispensing step including the steps of:

monitoring said parameter continuously using said at least one sensor, each said at least one sensor producing a parameter profile;

identifying an onset point associated with said parameter which can be measured by said at least one sensor, said onset point being determined by a first detectable change of said parameter in said parameter profile;

identifying an end point associated with said parameter, said end point being determined by a second detectable change in said parameter profile, thereby defining a specific time period; and measuring the displacement of said positive displacement element of said metering pump during the time period between said identified onset point and said identified end point, wherein said measurement provides a determination of dispensed liquid volume, wherein said at least one sensor includes at least one pressure transducer for measuring pressure changes in said metering probe and producing a pressure profile, said onset point relating to a change in said pressure profile indicative of a reduction in pressure in said metering probe that is further indicative of a meniscus of dispensed liquid first contacting said reaction vessel and the end point relating to an abrupt reduction in pressure according to said pressure profile occurring after the entire quantity of liquid has been dispensed from the metering probe.

2. A method as recited in claim 1, wherein said pump motor is a stepper motor, said measuring step including the step of counting the number of pulses of said pump motor between said onset point and said end point wherein each said pulse equates to a predetermined liquid quantity.

3. A method as recited in claim 1, wherein said reaction vessel is a slide element.

4. A method for dynamically determining the volume of a wash liquid dispensed by a metering system onto an immuno-rate slide element, said metering system including a metering pump, a pump motor and at least one sensor capable of continuously measuring a parameter of said metering system, said method including the steps of:

aspirating a quantity of wash liquid into a metering probe using said metering pump;

moving said metering probe relative to said slide element; and dispensing the quantity of liquid onto said slide element said dispensing step including the steps of:

identifying an onset point associated with a parameter which can be measured by said metering system by identifying a first detectable change in a monitored parameter profile as measured by said at least one sensor;

identifying an end point associated with said parameter by identifying a second detectable change in a monitored parameter profile as measured by said at least one sensor, thereby defining a specific time period; and counting the number of pulses of said pump motor, wherein each pulse of said pump motor is indicative of the dispensing of a predetermined amount of liquid, and totaling the number of pulses during the period between said identified onset point and said identified end point to determine total liquid volume during that period wherein said at least one sensor includes at least one pressure transducer for measuring pressure changes in said metering prone, said at least one pressure transducer measuring a first pressure change in said metering probe indicative of said identified onset point and a second pressure change in said metering probe indicative of said identified end point, wherein said first pressure change is indicative of a meniscus of liquid first contacting said slide element from said metering probe and said second pressure change is indicative of an abrupt reduction in pressure occurring after all liquid has been dispensed from said metering probe.

5. A method as recited in claim 4, wherein said metering system includes a conduit between said metering probe and said metering pump and said at least one sensor is disposed relative to said conduit for measuring said parameter.

* * * * *